(12) United States Patent
Kudugunti et al.

(10) Patent No.: US 11,339,775 B2
(45) Date of Patent: May 24, 2022

(54) ALTERNATING TANGENTIAL FLOW RAPID HARVESTING

(71) Applicant: Repligen Corporation, Waltham, MA (US)

(72) Inventors: Shashi Kiran Kudugunti, Waltham, MA (US); WengLong Roy Lin, Newton, MA (US); John Bonham-Carter, Somerville, MA (US); James R. Rusche, Framingham, MA (US)

(73) Assignee: Repligen Corporation, Waltham, MA (US)

( * ) Notice: Subject to any disclaimer, the term of this patent is extended or adjusted under 35 U.S.C. 154(b) by 163 days.

(21) Appl. No.: 15/659,562

(22) Filed: Jul. 25, 2017

(65) Prior Publication Data

US 2018/0148677 A1    May 31, 2018

Related U.S. Application Data

(60) Provisional application No. 62/366,557, filed on Jul. 25, 2016.

(51) Int. Cl.
| | |
|---|---|
| C12N 5/00 | (2006.01) |
| F04B 43/06 | (2006.01) |
| C07K 1/34 | (2006.01) |
| B01D 63/02 | (2006.01) |
| C12M 1/00 | (2006.01) |
| F04B 53/16 | (2006.01) |
| B01D 61/14 | (2006.01) |
| B01D 65/08 | (2006.01) |
| C12M 1/26 | (2006.01) |
| C07K 16/00 | (2006.01) |

(52) U.S. Cl.
CPC ............ *F04B 43/06* (2013.01); *B01D 61/145* (2013.01); *B01D 63/02* (2013.01); *B01D 65/08* (2013.01); *C07K 1/34* (2013.01); *C12M 29/04* (2013.01); *C12M 29/10* (2013.01); *C12M 29/16* (2013.01); *C12M 33/14* (2013.01); *C12M 47/10* (2013.01); *C12N 5/0018* (2013.01); *F04B 53/16* (2013.01); *B01D 2315/10* (2013.01); *B01D 2321/2083* (2013.01); *C07K 16/00* (2013.01); *C07K 2317/14* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 5,023,182 A | 6/1991 | Vail | |
| 6,544,424 B1 | 4/2003 | Shevitz | |
| 9,085,753 B2 | 7/2015 | Liu et al. | |
| 2010/0098725 A1* | 4/2010 | Liu | A61P 31/16 424/209.1 |
| 2014/0004097 A1* | 1/2014 | Zhang | C12Y 301/06013 424/94.6 |
| 2016/0068565 A1 | 3/2016 | Shibano et al. | |

FOREIGN PATENT DOCUMENTS

| | | | |
|---|---|---|---|
| CN | 103157102 A | 6/2013 | |
| CN | 103305417 A | 9/2013 | |
| WO | WO-2008152075 A1 * | 12/2008 | ............ C07K 16/00 |
| WO | WO 2012/045769 | 4/2012 | |
| WO | WO-2014073967 A1 * | 5/2014 | ............ C12M 23/58 |
| WO | 2015188009 A1 | 12/2015 | |
| WO | WO 2015/188009 | 12/2015 | |
| WO | WO 2017/082990 | 5/2017 | |

OTHER PUBLICATIONS

Kelly et al., "Understanding and Modeling Alternating Tangential Flow Filtration for Perfusion Cell Culture", Biotechnol. Prog., 2014, vol. 30, No. 6, pp. 1291-1300. (Year: 2014).*
'bioprocessintl.com' [online]. "A Decade of Harvesting Methods," Jun. 1, 2012 [retrieved on Oct. 25, 2017], Retrived from the Internet: URL http://www.bioprocessintl.com/downstream-processing/chromatography/a-decade-of-harvesting-methods-331186/. 7 pages.
International Search Report and Written Opinion in International Application No. PCT/US17/43797, dated Oct. 5, 2017, 14 pages.
Karst Daniel J. et al., "Characterization and comparison of ATF and TFF in stirred bioreactors for continuous mammalian cell culture processes." Biochemical Engineering Journal., Elsevier, Amsterdam, NL, 110, Feb. 3, 2016, 17-26.
Clincke M F et al., "Very high density of Chinese hamster ovary cells in perfusion by alternating tangential flow or tangential flow filtration in WAVE bioreactor ™—Part II: Applications for antibody production and cryopreservation," Biotechnology Progress, 29(3), May 21, 2013, 768-777.
Supplementary European Search Report dated Mar. 19, 2020 for European Patent Application No. 17835142.5.

* cited by examiner

*Primary Examiner* — Laura Schuberg
(74) *Attorney, Agent, or Firm* — KDB

(57) ABSTRACT

Methods and systems of harvesting a cell product from a cell culture by culturing cells in a fluid medium until the cells have produced a cell product at a harvest concentration are disclosed. The cells are cultured in a cell culture system including a bioreactor connected to an ATF device. The methods include draining fluid medium from the bioreactor through the outlet and the ATF device until the bioreactor volume reaches a predetermined volume, and the ATF column yields at an ATF outlet a liquid containing cell product and passes fluid medium with a concentration of cell product that is lower than the harvest concentration back into the bioreactor, extracting the liquid containing cell product from the ATF outlet, refilling the bioreactor with sterile phosphate buffered saline or fluid medium without any cell product, and repeating steps until a desired amount of cell product has been removed.

18 Claims, 11 Drawing Sheets

ALTERNATING TANGENTIAL FLOW RAPID HARVESTING

CROSS-REFERENCE TO RELATED APPLICATION

This application claims priority from U.S. Provisional Application No. 62/366,557, filed on Jul. 25, 2016, the entire contents of which are incorporated herein by reference.

FIELD OF THE INVENTION

The invention relates to the use of alternating tangential flow filtration units for harvesting products from bioreactors, e.g., for harvesting of products from fed-batch bioreactor cultures.

BACKGROUND

Cultures of microbial, plant, or animal cells are used to produce biological and chemical substances of significant commercial value. Particularly for commercial production, these cultures can be run in three operational modes: batch, continuous, fed-batch, or concentrated fed-batch. Applications include fermentation, biotechnology, and chemical, for production of specialty chemicals and products, as well as waste-treatment. The products are typically high-value products that include any desired cellular products, such as endogenous and recombinant products, including proteins, peptides, nucleic acids, virus, amino acids, antibiotics, specialty chemicals and other molecules of value. Desired proteins may include but are not limited to monoclonal antibodies, enzymes and other recombinant antibodies, enzymes, peptides, virus. Even marginal improvements in yield and productivity increase profitability. Therefore, there are incentives to improve batch, fed-batch, or concentrated fed-batch reactor operations.

Harvesting the products from a fed-batch bioreactor using current technology typically employs separation processes such as centrifugation and depth filtration, which can be time consuming and can generate lower product recovery than is desirable. Centrifugation has been part of cell harvesting for some time, but this process causes high shear, leading to low viability and potentially altered protein quality. Depth filtration has advantages over centrifugation, but has its own limitations such as the need for monitoring differential pressure, disposal of filters, large footprints, and scale-up issues. In addition, both centrifugation and depth filtration suffer from requiring a second clarification step to produce a fluid suitable for chromatographic separation processes.

SUMMARY

The methods and systems described in this disclosure are based, at least in part, on the discovery that alternating tangential flow (ATF) filtration can be adapted to perform rapid harvesting from a cell culture, such as a fed-batch culture or a concentrated fed-batch culture, to achieve the beneficial result of rapid, high-yield harvesting of cell products. The use of ATF for harvesting fed-batch and other types of cell cultures allows for a rapid harvest procedure carried out with minimal steps, because the new methods simplify the harvest procedure, which generally requires two or more steps such as centrifugation and depth filtration. ATF harvesting results in a feed stream suitable for the next stage, e.g., a chromatography column, with high clarity and thus avoids fouling of downstream systems. Accordingly, the present disclosure describes a series of methods for harvesting fed-batch and concentrated fed-batch cultures using ATF.

It is common to use centrifugation or depth filters to harvest the protein from fed-batch bioreactors. However, the recovery of protein using these common technologies is low, and is a time consuming process. According to the new methods and systems described herein, the use of ATF as rapid harvesting equipment on a fed-batch bioreactor can reduce the harvesting time to less than 8 or 10 hours. The new methods also maintain the protein quality, because the cell viability remains high through the entire process of harvesting.

In a first aspect, the present disclosure includes methods of harvesting a cell product from a cell culture, e.g., a fed-batch or concentrated fed-batch cell culture. Cell products include any desired endogenous and recombinant proteins, nucleic acids, viruses, and other molecules of value. Desired proteins may include, but are not limited to, monoclonal antibodies, enzymes, and other recombinant or naturally occurring proteins. The methods include culturing cells in a starting volume of culture medium until the cells have produced a cell product at a harvest concentration in the culture medium, wherein the cells are cultured in a cell culture system including a bioreactor connected to an alternating tangential flow (ATF) device; draining culture medium from the bioreactor through the ATF device until the culture medium volume reaches a predetermined volume, wherein the ATF device provides at an ATF outlet a liquid containing cell product and returns to the bioreactor culture medium with a concentration of cell product that is lower than the harvest concentration; extracting the liquid containing cell product from the ATF outlet; refilling the bioreactor with a fluid medium to a volume that is equal to, higher than, or lower than the starting volume; and repeating one or more of the draining, extracting, and refilling steps until a desired amount of cell product has been removed from the bioreactor.

In these methods, the predetermined volume can be lower or higher than the starting volume, or about the same as the starting volume. The fluid medium used to refill the bioreactor can be phosphate buffered saline (PBS), or cell culture medium, or any other liquid that can be used to maintain the cells alive.

In some implementations, the refilling includes simultaneously refilling the bioreactor at a rate equal to the rate of draining of the culture medium from the bioreactor or at a rate of extracting the liquid from the ATF outlet. In certain embodiments, the draining step and the refilling step are performed sequentially, and/or the refilling step and draining step are performed two or more times.

In the new methods, the harvest can takes less than 18 hours, e.g., less than 24, 20, 18, 16, 14, 12, 10 hours, or less, e.g., less than 9, 8, 7.5, 7.0, 6.5, 6.0, 5.5, or 5.0 hours, or less, for a volume between 500 liters and 2000 liters. For example, in some embodiments, repeating both the draining step until the bioreactor volume reaches a predetermined volume and the extracting step can take less than 2.5 hours. In certain embodiments, the culture medium is drained at a filter flux of about 2 to 30 liters/meter$^2$/hour (LMH), e.g., about 2, 4, 5, 6, 7, 8, 9, or 10 to 30 liters/meter2/hour (LMH), e.g., 3 to 25, 4 to 20, or 5 to 15 LMH.

In various implementations, the predetermined volume can be about 5% to about 30% of the starting volume or about 10% to about 20% of the starting volume. In these methods, the cell culture can be a concentrated fed-batch culture, and the predetermined volume can be about 50% of the starting volume or 100% of the starting volume. In some embodiments, the predetermined volume is determined based on a cell concentration in the culture medium.

In some implementations, the ATF device can include a hollow fiber filter, e.g., having a pore size of about 0.1 to 5.0 microns, e.g., 0.2, 0.3, 0.4, 0.5, 0.6, 0.7, 0.8, or 0.9 microns, or 1, 2, 3, or 4 microns, or about 500 to 1000 kD, e.g., 550, 600, 650, 700, 750, 800, 850, 900, or 950 kD.

In these methods, any two or more of the draining step, the extracting step, and the refilling step can occur simultaneously and at a first flow rate. For example, any one or more of the draining step, the extracting step, and the refilling step can be started before the cells have produced all of the cell product to be harvested at the conclusion of cell culture process. In some embodiments, the draining step, the extracting step, and the refilling step are started 1 to 8 days, e.g., 2 to 7 days or 3 to 6 days, before the cells have produced the cell product at the harvest concentration in the fluid medium.

In some embodiments, the extracting and refilling volume are less than about 1.0, e.g., less than about 0.9, 0.8, 0.7, 0.6, 0.5, 0.4, 0.3, 0.2, or 0.1 vessel volume exchanged per day (VVD).

In some implementations, a final harvesting step is conducted at a second flow rate different from the first flow rate. In some embodiments, a final draining step can result in less than about 20%, e.g., less than 10%, of the starting volume remaining in the bioreactor.

In all of these methods, the cell culture can be a fed-batch cell culture or a concentrated fed-batch cell culture, and the methods can be used to produce cell products such as monoclonal antibodies, enzymes, and/or viruses.

In another aspect, the disclosure provides systems for harvesting a cell product from a cell culture. These systems include a bioreactor including an inlet and an outlet; a source of cell culture medium containing no cell product connected to the bioreactor inlet; an alternating tangential flow (ATF) device connected to the bioreactor outlet; a pump connected to an outlet from the ATF device and configured to remove fluid from the ATF device; and a controller arranged and programed to carry out one or more of the methods described herein, either singly or in various combinations and subcombinations.

The methods and systems described in this disclosure provide several advantages, including maintaining high cell viability and better protein quality in the products harvested using the new methods described herein, because of low shear during harvest of fed-batch cultures. Cell death or stress often leads to release of protein degrading or modifying enzymes, which can compromise product quality. The new methods and systems result in higher yields and increased productivity with improved protein quality. The new methods and systems allow recovery of the cell broth with the cells largely intact and in an unadulterated form and do not impair the subsequent separation performance of or increase risk of increasing unwanted biologics during the harvest of and separation of the cultured cells from their liquid media. The rate of protein passage through the membrane is important to complete the separation step quickly. Production time using the new methods and systems represents an economic advantage and also can be required to obtain unstable proteins quickly to avoid unwanted product modifications such as degradation.

"Fed-batch culture" refers to an operational technique for biotechnological processes where one or more nutrients necessary for cell growth and product formation are fed or supplied to the bioreactor during cultivation either intermittently or continuously via one or more feed streams during the course of an otherwise batch operation. There are no effluent streams during the course of operation, so the bioreactor products remain in the bioreactor until the end of the run when they are harvested. This process may be repeated a number of times if the cells are fully viable and productive. Fed-batch cultures are advantageous since the fed-batch operation can provide unique means of regulating the concentration of compounds that control the key reaction rates and, therefore, can provide a definite advantage over the batch operation through the manipulation of one or more feed rates. Fed-batch culture is also advantageous for large-scale production due to its operational simplicity and familiarity as a carryover process from fermentation.

The term "depth filtration" refers to filtration that uses a porous filtration medium to retain particles throughout the medium, rather than just on the surface of the medium. Such filters are commonly used when the fluid to be filtered contains a high load of particles as, they can retain a large mass of particles before becoming clogged compared to other types of filters. Depth filtration is typified by multiple porous layers whose depth are used to capture solid contaminants from the liquid phase.

The term "diafiltration" refers to a dilution process that involves removal or separation of components (e.g., permeable molecules like salts, small proteins, solvents etc.,) of a solution based on their molecular size by using micromolecule permeable filters in order to produce pure solution. This is often performed by removing filter permeate at the same rate as adding liquid to the solution being filtered (termed constant volume diafiltration).

The term "cell broth" refers to the liquid in which the cells are suspended during culture. In a fed-batch process this includes both the fed media and nutrients, as well as the cell products (e.g., proteins and waste).

The term "concentrated fed-batch" (CFB), refers to use of a perfusion system (Alternating Tangential Flow (ATF)/ Tangential Flow Filtration (TFF)) with an ultrafiltration membrane (e.g., 50 kDa or 30 kDa nominal MW cutoff) that retains the protein product in the bioreactor while removing waste products and feeding additional media into the reactor vessel. This process obtains higher cell concentration and retains product in the reactor like a conventional fed batch process.

The term "continuous feeding" refers to the continuous addition of media or media components to the bioreactor for some portion of the harvest period.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 8 is a flow chart of a method for performing the rapid ATF fed-batch harvest of FIG. 7.

DETAILED DESCRIPTION

Figure 1:
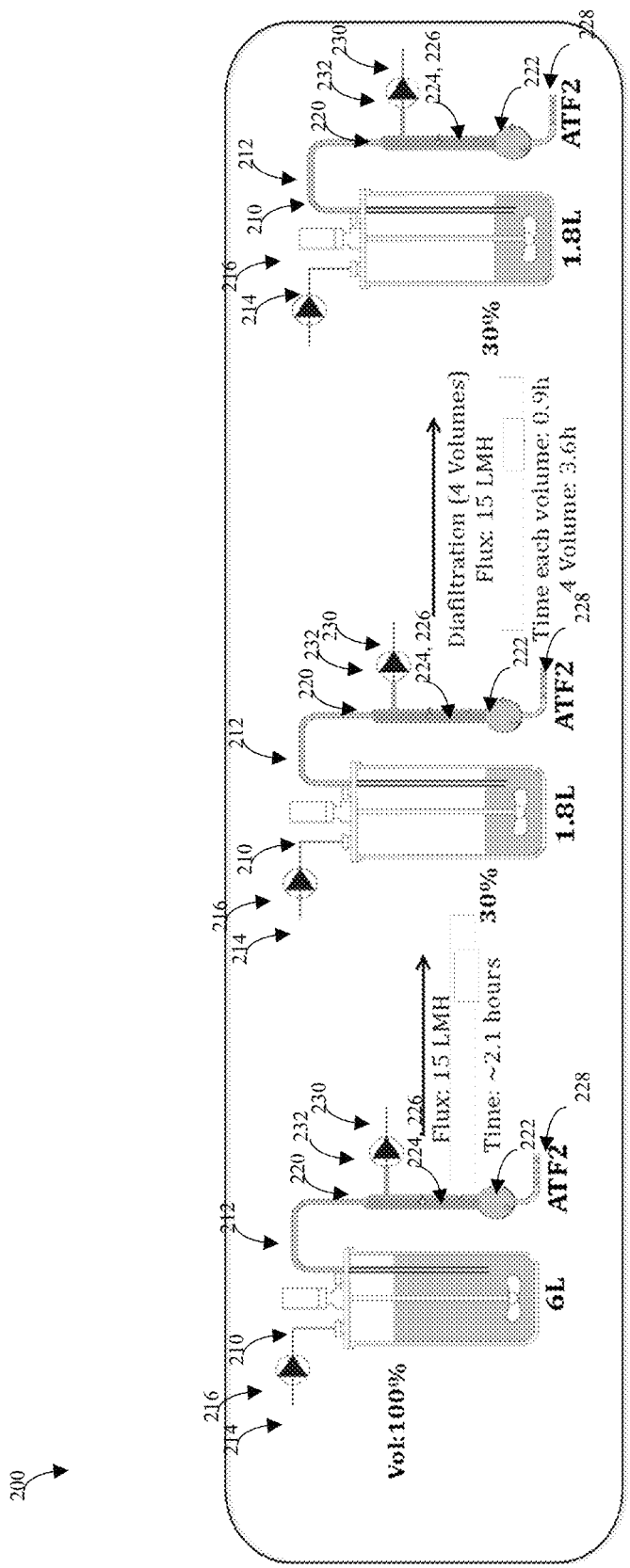
FIG. 1 is schematic of an apparatus and process for performing rapid ATF fed-batch harvest.

The present disclosure describes the use of alternating tangential flow (ATF) filtration for performing fed-batch harvesting. The use of ATF for harvesting fed-batch cultures allows for a rapid harvest procedure carried out in a single process step, processing a batch with a single set of equipment with a single product as a processed material. These methods are successful when using ATF, compared to other tangential flow filtration methods due to the ability to perform product harvesting at a higher filter flux with ATF.

Alternating tangential flow (ATF) has been used to perform filtration and separate cells from product in a single step, but is normally limited to a filter flux of 1.3-5.7 LMH, which is too slow to be useful in a commercial culture harvest setting. Unexpectedly, when ATF filtration was performed at a higher flux (e.g., greater than 10 LMH) as described herein, the filter did not foul and a rapid recovery of product from a culture was obtained in a short processing time. This rapid harvest of a culture with ATF has utility in commercial processes as an economically advantageous way to obtain a clarified feed stream suitable for further processing in a single step.

The new methods also simplify the harvest procedure, which heretofore has generally required two or more steps such as centrifugation followed by depth filtration. ATF harvesting as described herein results in a feed stream that can be used directly in the next stage, e.g., to a chromatography column, with high clarity and thus avoids downstream fouling, e.g., of the chromatography column, without the need for any other filtration or other clarification step.

During fed-batch culture, biotechnological processes are leveraged to create a desired product. During the culture, one or more nutrients necessary for cell growth and product, this may include, for example, any desired cellular product including endogenous and recombinant products including proteins, nucleic acids, virus, and other molecules of value, formation are fed or supplied to the bioreactor during cultivation. This feeding is performed either continuously or intermittently via one or more feed streams during the course of an operation. There are no effluent streams during the course of operation, so the volume of liquid and cells within the bioreactor increases during the operation. The bioreactor products remain in the bioreactor until the end of the run when they are harvested, typically after 5 to 30 days, e.g., 7 to 25, or 10 to 21 days of culture. Harvesting of fed batch cultures is best performed with little damage to cells in the broth, rapidly to provide efficient processing without product modification and with clarification needed for further processing of a product by chromatography. ATF is uniquely able to support these requirements.

Historically, ATF has been used in perfusion culture systems in which cell media is continually supplied to the bioreactor containing the cells and the ATF continually filters the culture, removing culture waste materials and protein product using a microfiltration membrane. This process allows protein to be harvested continuously or at frequent intermittent intervals, and at low filter flux (1.3-5.7 LMH) for the cultivation period that lasts 30 days or even longer. This process is carried out at high cell densities (e.g., 50-150E6 cells % mL or higher). These ATF assisted perfusion cultures can also be performed with an ATF containing an ultrafilter (e.g., nominal pore size 50 kD or smaller) during which waste materials are removed but the product is retained within the culture broth. These cultures are operated at a low filter flux. These are sometimes referred to as concentrated fed batch (CFB) as the desired cellular products are retained in the cell broth as removal of waste products permits a much higher concentration of cells and therefore a higher concentration of desired product.

In the present methods, rather than using ATF at a low flux continual cell culturing, the ATF process is instead adapted to serve as rapid harvesting equipment (replacing depth filtration and centrifugation) on a fed-batch culture. In the new processes, ATF is used differently with a high filter flux on the day of harvesting the fed-batch culture, with cell densities that usually range from 7-20E6 cells/ml or a CFB culture with cell densities ranging from 50-200E6 cells/ml (e.g., between 75-120E6 cells/ml). Unlike a traditional perfusion system, in the new processes the product, e.g., protein, is harvested at a high filter flux. The use of an ATF system as rapid harvesting equipment on a fed-batch or CFB bioreactor can overcome the aforementioned issues as this entire harvesting process maintains high cell viability and better product quality.

The methods are embodied in four different rapid harvesting techniques for fed-batch and concentrated fed-batch bioreactors that include:

(1) ATF rapid harvesting using step-diafiltration (for traditional fed-batch cultures), (2) ATF rapid harvesting using continuous-diafiltration (for traditional fed-batch cultures; more efficient and less time consuming than step-diafiltration), (3) ATF rapid harvesting using continuous diafiltration (for concentrated fed-batch cultures; more efficient and less time consuming), and (4) ATF rapid harvesting with continuous feeding (more efficient and less time consuming with increased protein yield). The procedures for these four different methods are described in greater detail below.

Rapid Harvest Using Step-Diafiltration

An ATF system with a hollow fiber porous membrane (e.g., microfiltration pore sizes such as 0.1-5.0 micron or ultrafiltration membranes such as 750 kDa MWCO) is well suited for harvesting a fed-batch culture because it retains cells and also other small particulates, which are necessary to remove before downstream processes. Using ATF also reduces cross-contamination as the harvesting can be carried out in a sterile manner, unlike centrifugation or depth filtration.

As shown in FIG. 1, an ATF harvest bioreactor system 200 includes a bioreactor 210, which can be, for example, a stirred tank reactor. The bioreactor 210 is connected via a drain tube 212 to an ATF 220. The ATF is a system such as ones used to perfuse a bioreactor culture using hollow fiber filtration using alternating tangential flow. The ATF 220 includes a device that controls a diaphragm pump 222 to perform ATF through a hollow fiber filter 224 (see, e.g., U.S. Pat. No. 6,544,424) both of which are encased in a sterilizable housing 226.

Figure 6:
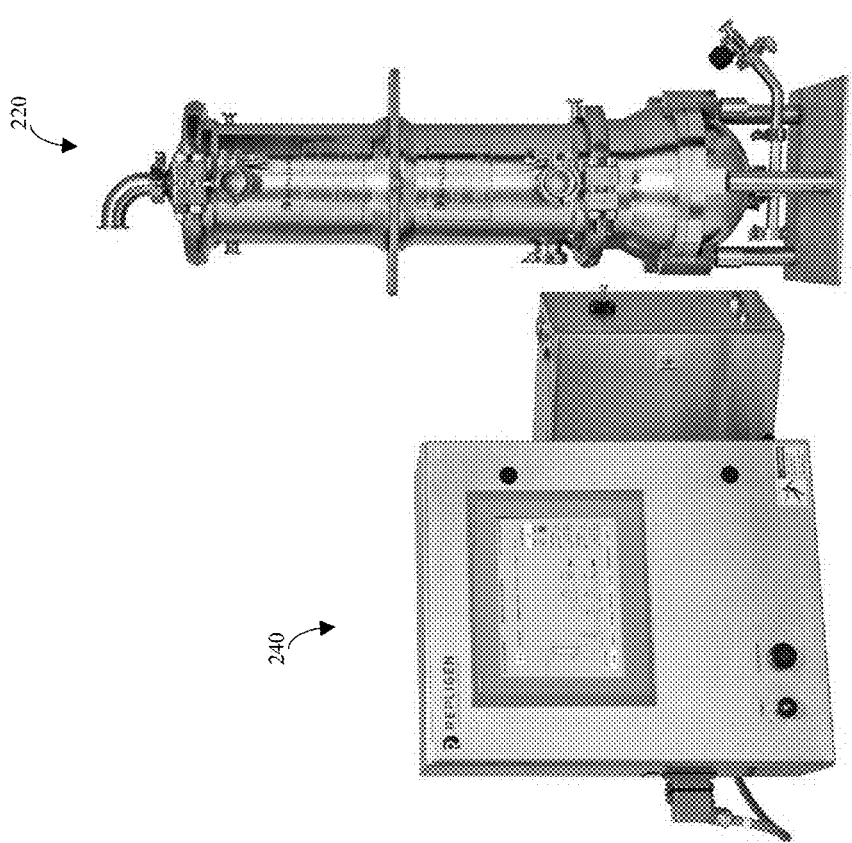
FIG. 6 is an overall system diagram for performing rapid ATF fed-batch harvest.

Medium and additives are introduced into the bioreactor 210 via a feed line 214, which is controlled by a valve and/or pump 216. An air supply source and the controller 240 (FIG. 6) are connected to the diaphragm pump 222 via an air tube 228. Air is added and withdrawn from the diaphragm pump 222 so as to increase and decrease the volume of the two chambers contained within the diaphragm pump, altering the pressure within the housing 226 and directing flow of the fluid contained within the housing 226 and drawing fluid across the membrane of the hollow fiber filter 224. Typically, the interior portion of the hollow fibers is fluidly connected to the bioreactor via drain tube 212 while the chamber outside the hollow fibers of the hollow fiber filter 224 and within the housing 226 is fluidly connected to a product drain tube 230. The product drain tube 230 has a harvest pump/valve 232 that controls withdrawal of the products that filter across the hollow fiber filter and reside in the chamber between the hollow fiber filter 224 and housing 226. In FIG. 1, the product drain tube 230 is shown near the top of the ATF 220, however the product drain tube 230 could also be located near the middle or bottom of the ATF 220. Alternatively, there may be more than one product drain tube 230 connected to the housing 226.

To carry out the rapid harvest using the ATF harvest bioreactor system 200, the product (e.g., the protein) is harvested using ATF at a rapid flux greater than 10 but not greater than 30 liters/meter$^2$/hour (LMH) (for example from 12-18 LMH, 13-16 LMH, or 15 LMH). The rapid harvest can be accomplished by cyclical removal of volume from the culture vessel and refilling (batch filtration) or by continually replenishing the liquid in the culture broth while harvesting liquid through the filtration process (constant volume diafiltration). Both approaches are described below and in the specific examples. It is practical in most bioreactor designs to only be able to remove approximately 80% of the volume and still maintain adequate stirring thus while some reactors may allow greater than 80% most generally, removal of 80% or less in the batchwise or cyclical method of filtration will be described.

For a 500 L amount of medium in a 600 L bioreactor (shown as 6 L in FIG. 1), the 15 LMH flux results in a drain time of approximately 2.1 to 2.5 hours in the present methods (assuming an ATF filter size of 11 m$^2$). This draining of the protein continues until the remaining volume in the bioreactor 210 volume drops down to, for example, 30% although other volume decrease values can be used (e.g., 20%). At this bioreactor volume, the harvest pump 232 is paused. The cells all remain in the bioreactor 210 and are within a media broth that is then filled to approximately the same amount of fluid as at the initiation of the harvest. In some instances, the media broth is then filled to a lower amount or a greater amount of fluid as the initiation of the harvest. The fluid could be sterile phosphate buffered saline (PBS) or culture media or other fluid compatible with a viable cell broth. The harvesting drain process resumes at flux of approximately 15 LMH until the volume in the bioreactor 210 again drops to approximately 30%. This cycle is repeated a third and fourth time, if desired or required. Approximately 96% of protein from the fed-batch culture originally contained within the bioreactor 210 is recovered and cell viability maintained.

Figure 2:
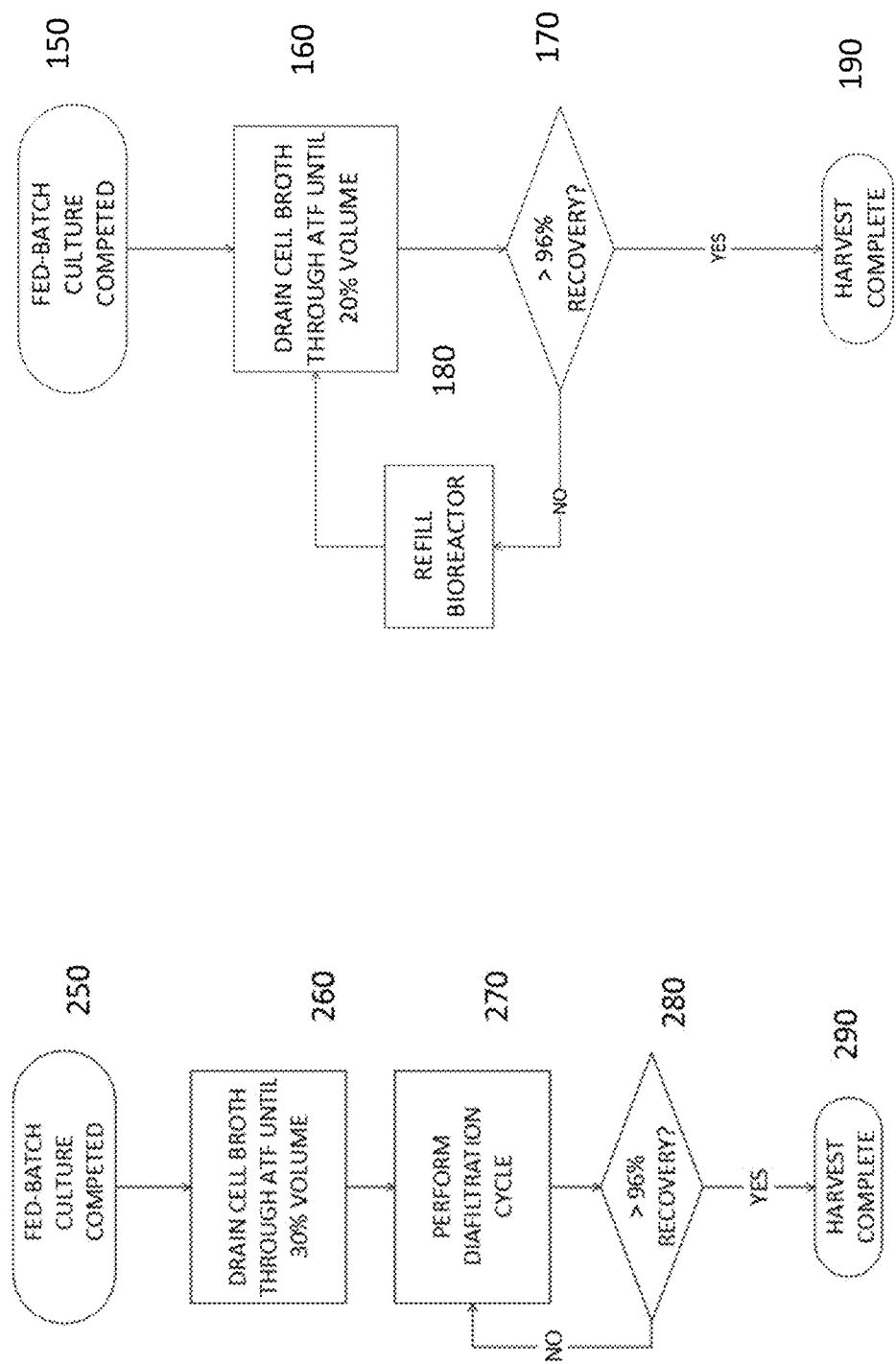
FIG. 2 is a flow chart of a method for performing the rapid ATF fed-batch harvest of FIG. 1.

The steps of the rapid harvest procedure are summarized in FIG. 2. When the fed-batch culture has completed, harvest starts at step 150. The harvest is carried out using ATF to drain the cell broth at a flux between 10-30 LMH (e.g., 15 LMH) until the volume of the bioreactor 110 is reduced to 10-50% or more preferably 20-30% of its initial volume, step 160. At this bioreactor volume, the harvest pump 232 is paused, and the operator determines whether the desired recovery has been achieved at step 170. This can be measured by number of drain/refill cycles (e.g., 2 or 3) or other means such as assaying the total amount or concentration of the harvested product. If the harvest is to continue, the bioreactor 210 is refilled at step 180, returning to the drain step 160 and ultimately to harvest completion at step 190.

Rapid Harvest Using Continuous Diafiltration

Figure 7:
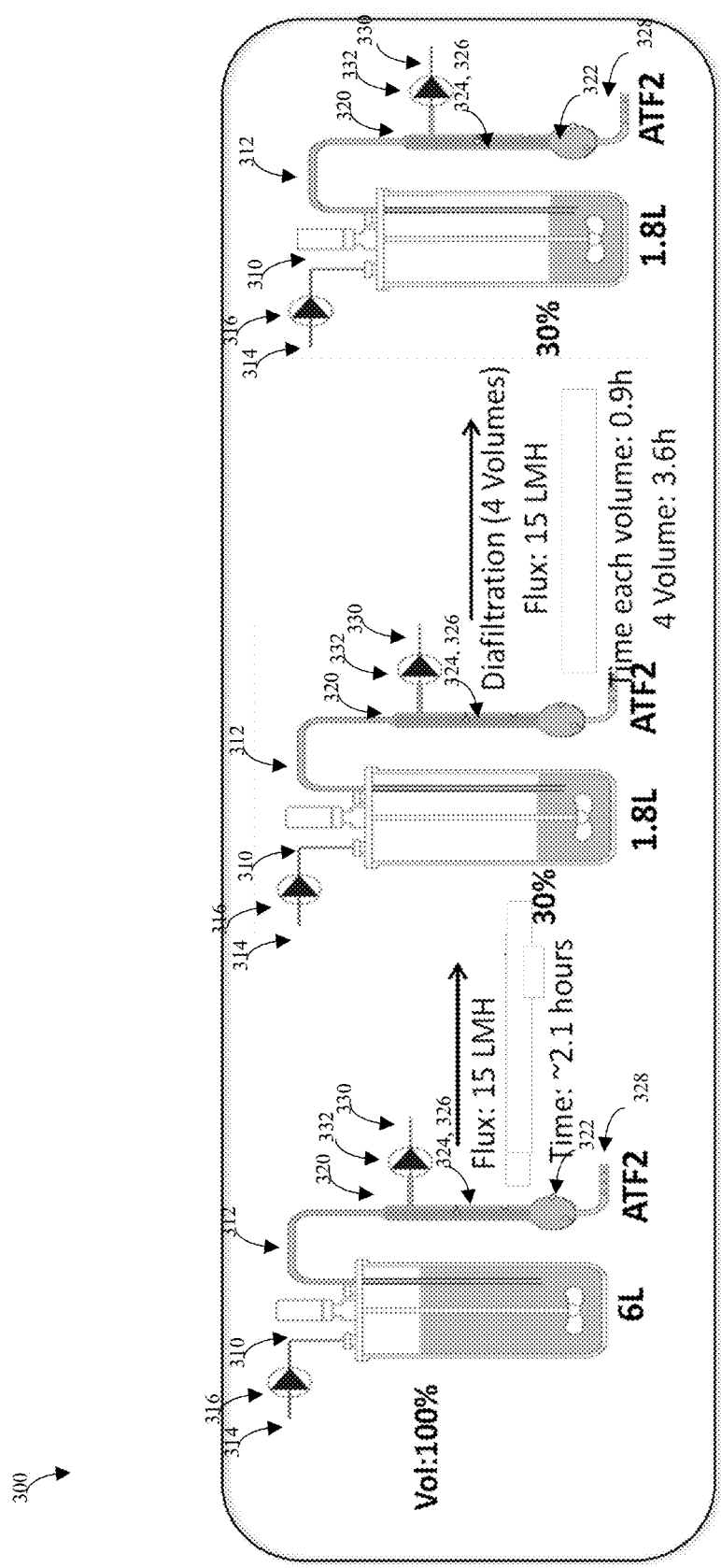
FIG. 7 is schematic of an apparatus and process for performing rapid ATF fed-batch harvest with continuous diafiltration.

In another embodiment, a rapid ATF harvest procedure using continuous diafiltration is shown in FIG. 7. This method of constant volume diafiltration, in some instances, provides a higher yield with less volume than the batchwise method. Testing for both methods for yield and time could be carried out to choose the best method for a given application. The components for harvesting with ATF continuous diafiltration are similar to those shown in FIG. 1. For this procedure, the ATF harvest bioreactor system 300 includes a bioreactor 310 connected via a drain tube 312 to an ATF 320. The ATF 320 includes a device that controls a diaphragm pump 322 to perform ATF through a hollow fiber filter 324 both of which are encased in a sterilizable housing 326.

Medium and additives are introduced to the bioreactor 310 via a feed line 314, which is controlled by a valve and/or pump 316. An air supply source and controller (not shown) are fluidly connected to the diaphragm pump 322 via an air tube 328. The interior portion of the hollow fibers (retentate) is connected to the bioreactor 310 via drain tube 312 while the chamber outside the hollow fibers of the hollow fiber filter 324 and within the housing 326 is connected to a product drain tube 330 (permeate). The product drain tube 330 has a harvest pump/valve 332 which controls withdrawal of the products within the permeate.

In this process, the protein is also harvested using the ATF 320 at a flux of 10-30 LMH (generally 12-18 or 15 LMH) until the volume of the bioreactor 310 drops down to a volume in which the elevated flux can be maintained for up to 4 bioreactor volumes of fluid transfer by filtration. The percentage of volume reduction may be 0-100%, for example, 30% for fed batch cultures or 0-50% for CFB cultures. In some instances, the percentage of volume reduction is, for example, 10-90%, e.g., 25-75%, e.g., 30-60%, e.g., 5, 10, 15, 20, 25, 30, 25, 30, 35, 40, 45, 50, 55, 60, 65, 70, 75, 80, 85, 90, 95, or 100%. For a 500 L bioreactor 310, the 15 LMH flux through an 11 m$^2$ filter results in a drain time to the 30% level of approximately 2.1 hours.

Once having reached this reduced bioreactor volume (e.g., 1.8 L), a diafiltration process is started to maintain the bioreactor volume by either addition of PBS or culture media (or other fluid compatible with maintaining cell viability) via the feed line 314 at flow rate equivalent to the fluid harvest rate via the product drain tube 330 (the permeate). This diafiltration process can occur at a flux of, for example, 15 LMH until the yield of desired product in the permeate reaches greater than 90%. Rapid harvesting by this method is therefore completed in less than approximately 6-8 hours (e.g., less than 6 hours).

Using either batchwise washing with collection of the permeate or constant diafiltration the rapid harvest of product from a fed batch or CFB culture can be achieved.

The steps of the rapid harvest procedure using continuous diafiltration are summarized in FIG. 8. When the fed-batch culture has completed, harvest starts at step 250. The harvest is carried out using ATF to drain the cell broth at a flux of from 10-30 LMH (e.g., 15 LMH) until the volume of the bioreactor 310 is approximately 30% its initial volume, step 260. At this bioreactor volume, the flow rate of the harvest pump 332 is reduced while fluid is added to the bioreactor 210 via the feed line 214 at approximately the same rate (e.g., 15 LMH) to complete a diafiltration cycle, step 270. Once a diafiltration cycle is complete by cycling through an entire displaced volume it is decided (at step 280) if the harvest is to continue (e.g., not yet 90% or 96% recovery) and the system returns to step 270 to perform an additional diafiltration cycle. Once the desired volume has been achieved the harvest operation is completed at step 290.

Rapid Harvest Using Continuous-Diafiltration for Concentrated Fed-Batch

Figure 12:
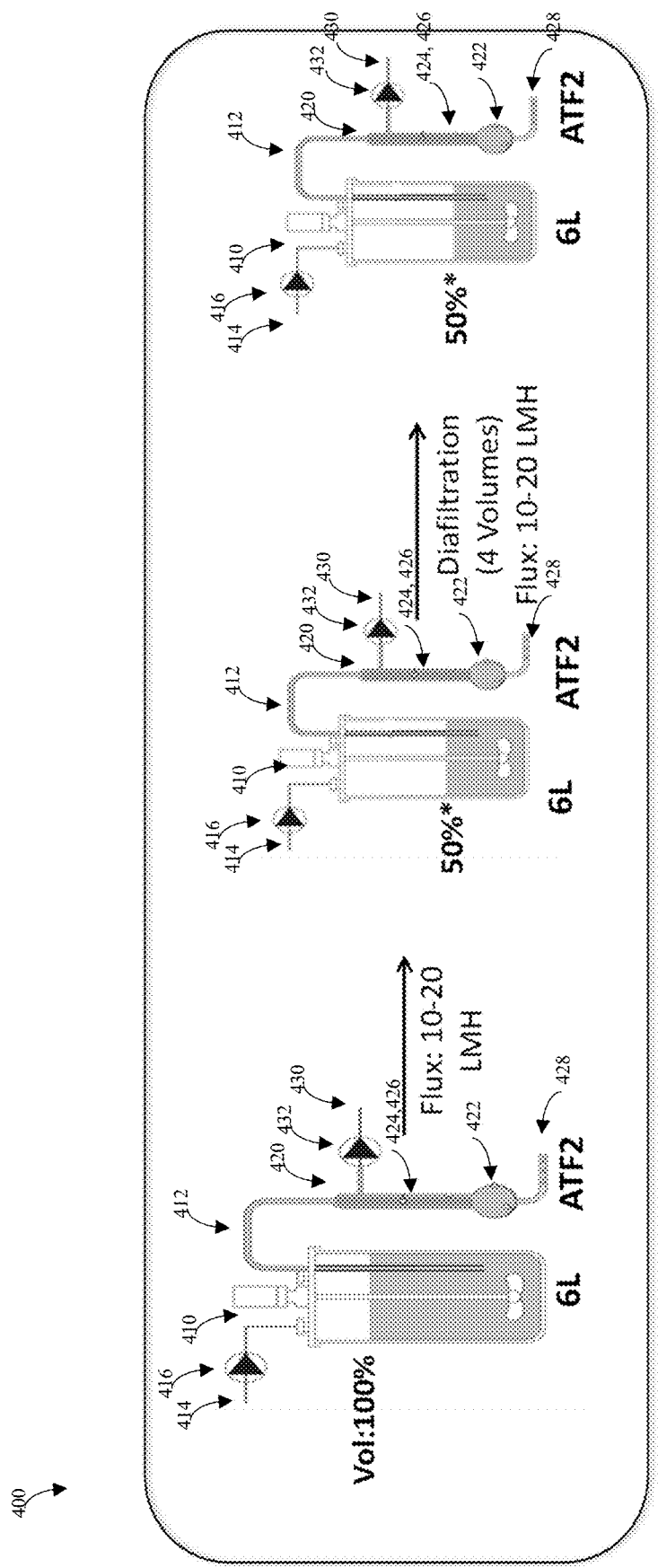
FIG. 12 is a schematic of an embodiment and an apparatus and process for performing rapid ATF concentrated fed-batch harvest with continuous diafiltration.

In another embodiment, a rapid ATF harvest procedure using continuous diafiltration for concentrated fed-batch systems is shown in FIG. 12. The process of ATF rapid harvest for concentrated fed-batch (CFB) depends on viable cell density on the day of harvest. The components for harvesting with ATF continuous diafiltration are similar to those shown in FIG. 1.

As shown in FIG. 12, an ATF harvest bioreactor system 400 includes a bioreactor 410, which can be, for example, a stirred tank reactor. The bioreactor 410 is connected via a drain tube 412 to an ATF 420. The ATF is a system such as ones used to perfuse a bioreactor culture using hollow fiber filtration using alternating tangential flow. The ATF 420 includes a device that controls a diaphragm pump 422 to perform ATF through a hollow fiber filter 424 (see, e.g., U.S. Pat. No. 6,544,424) both of which are encased in a sterilizable housing 426.

Medium and additives are introduced into the bioreactor 410 via a feed line 414, which is controlled by a valve and/or pump 416. An air supply source and controller (not shown) are fluidly connected to the diaphragm pump 422 via an air tube 428. Air is added and withdrawn from the diaphragm pump 422 so as to increase and decrease the volume of the two chambers contained within the diaphragm pump, altering the pressure within the housing 426 and directing flow of the fluid contained within the housing 426 and drawing fluid across the membrane of the hollow fiber filter 424. Typically, the interior portion of the hollow fibers is fluidly connected to the bioreactor via drain tube 412 while the chamber outside the hollow fibers of the hollow fiber filter 424 and within the housing 426 is fluidly connected to a product drain tube 430. The product drain tube 430 has a harvest pump/valve 432 that controls withdrawal of the products that filter across the hollow fiber filter and reside in the chamber between the hollow fiber filter 424 and housing 426.

In FIG. 12, the product drain tube 430 is shown near the top of the ATF 420, however the product drain tube 430 could also be located near the middle or bottom of the ATF 420. Alternatively, there may be more than one product drain tube 430 connected to the housing 426.

If the viable cell density (VCD) is below 100E6 cells/mL on the day of harvest at the end of concentrated fed-batch bioreactor 410 culture, the protein is harvested using the ATF 420 at a flux of 10-30 LMH (generally 12-18, 13-16, or 15 LMH) until the volume of the bioreactor 410 drops down to a volume in which the elevated flux can be maintained for up to 4 bioreactor volumes of fluid transfer by filtration. This may be 0-50%, for example 50%, depending on the cell density.

Once having reached this reduced bioreactor volume a continuous diafiltration process is started to maintain the bioreactor volume by either addition of PBS or culture media (or other fluid compatible with maintaining cell viability) via the feed line 414 at flow rate equivalent to the fluid harvest rate via the product drain tube 430 (the permeate). This diafiltration process can occur at a flux of, for example, 10-30 LMH until the yield of desired product in the permeate reaches greater than 90%. Rapid harvesting by this method is therefore completed in less than approximately 6-8 hours (e.g., less than 6 hours).

Figure 13:
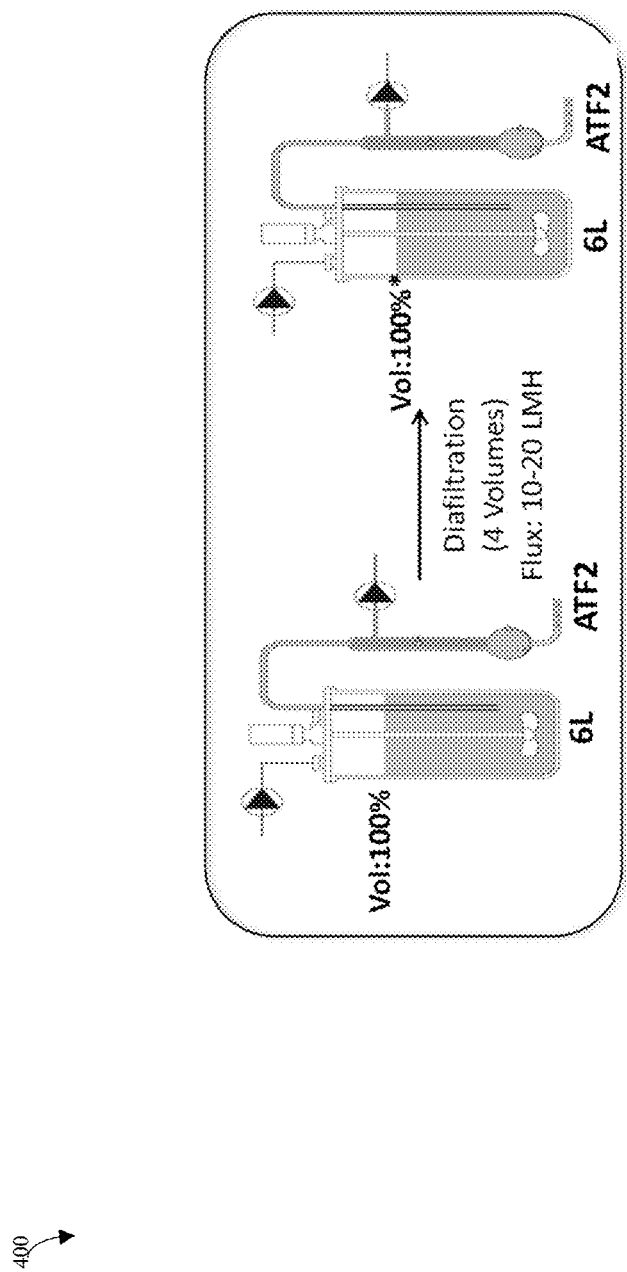
FIG. 13 is a schematic of an embodiment of an apparatus and process for performing rapid ATF concentrated fed-batch harvest with continuous diafiltration.

It is recommended not to concentrate the cell density when the VCD is already above 100E6 cells/mL on the day of harvest. Referring to FIG. 13, in this case there will be no reduction in bioreactor volume before continuous diafiltration. A continuous diafiltration process is started to maintain the bioreactor volume at 100% by either addition of PBS or culture media (or other fluid compatible with maintaining cell viability) via the feed line 414 at flow rate equivalent to the fluid harvest rate via the product drain tube 430. This diafiltration process can occur at a flux of, for example, 10-30 LMH until the yield of desired product in the permeate reaches greater than 90%, e.g., after 4 bioreactor volume exchanges. After 4 volume exchanges the remaining media will be harvested in exchange with either PBS or fresh media.

The following Table 1 shows a suggested reduction in bioreactor volume depending on the cell density on the day of harvest (which can be determined by known measurement techniques).

TABLE 1

Bioreactor Volume Management

| VCD (10e6 Cells/mL) | % Reduction in BR volume | Flux (LMH) |
|---|---|---|
| <30 | 10%-30% | 10-30 |
| 50-100 | 0%-50% | 10-30 |
| >100 | 0% | 5-30 |

These methods provide a new way to operate cell bioreactor harvest in which an ATF instrument is operated at an increased flux from normal operation. This unique approach can attain rapid harvest that was not possible before. The features of this process are: a single process step to attain a particle free feed stream and the speed at which product harvest can occur. These features provide significant economic benefit in biologic manufacturing processes due to reduced processing time and reduced equipment costs for multiple processing steps.

ATF Rapid Harvest Using Continuous Feeding

A fed-batch with continuous feeding and rapid harvest process was developed to further shorten the harvesting time. This technique both shortens the harvest time by half and increases protein production while maintaining cell viability to assure high product quality. Increased protein production during harvest is not achievable by currently existing commercially available fed-batch harvest techniques. The increased productivity is especially advantageous since it is accomplished without a change in basic equipment used in fed batch culturing such as the bioreactor or control systems for cell culture.

Continuous slow feeding of a fed-batch bioreactor during the final days of cultivation boosts the protein production without adding additional time to the fed-batch cultivation and harvest processes. This can be accomplished using either a microfilter (collection of the product in the permeate) or with an ultrafilter (retention of the product in the reactor where it will be collected during the final harvest stage). Moreover, the continuous harvest process also increases the viability of a fed-batch culture, which is favorable to protein quality. This process reduces cross contamination as the entire process is conducted in a sterile manner, unlike centrifugation or depth filtration.

Figure 14:
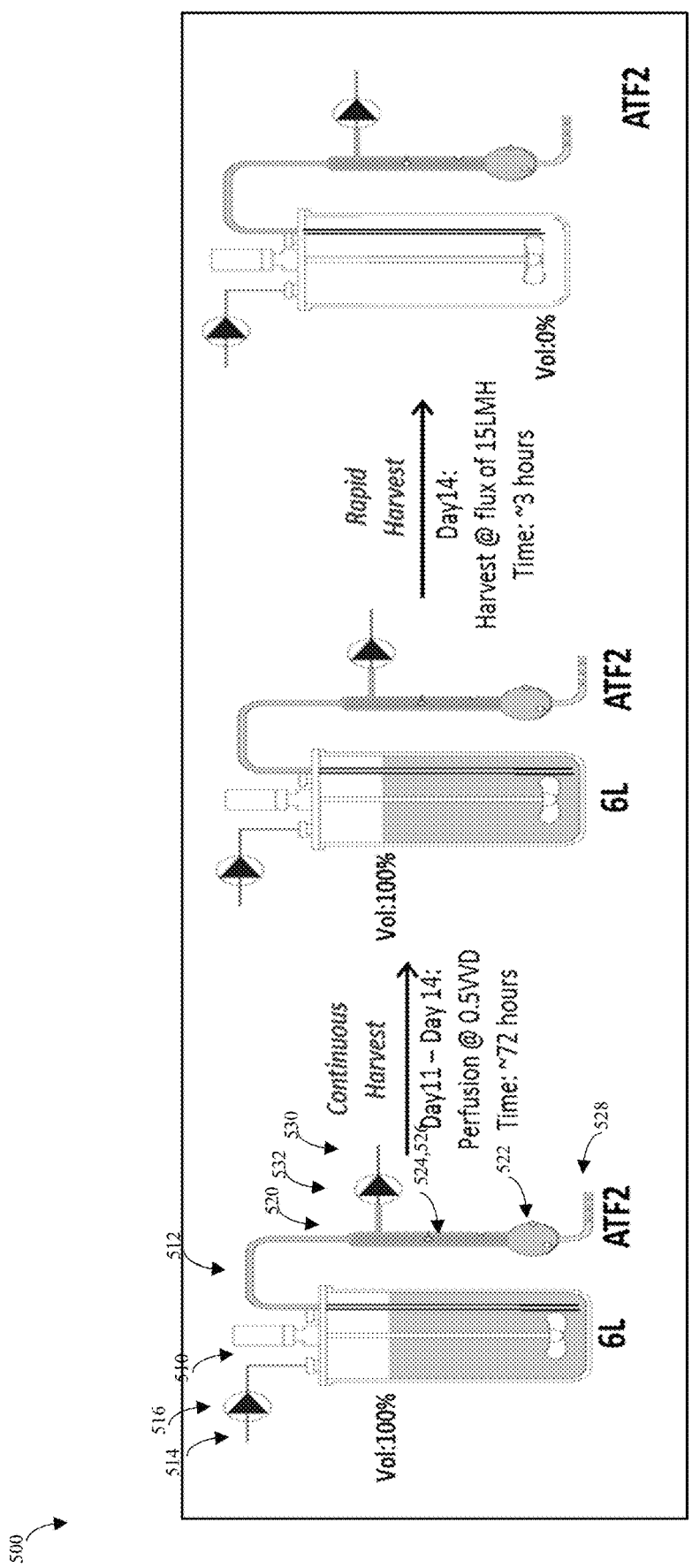
FIG. 14 is a schematic of an embodiment of an apparatus and process for performing rapid ATF fed-batch harvest with continuous feeding followed by rapid harvest.

FIG. 14 shows a schematic for the apparatus for use with the fed-batch with continuous feeding & rapid harvest using ATF method. The components for harvesting with ATF continuous diafiltration are similar to those shown in FIG. 1.

As shown in FIG. 14, an ATF harvest bioreactor system 500 includes a bioreactor 510, which can be a stirred tank reactor. The bioreactor 510 is connected via a drain tube 512 to an ATF 520. The ATF 520 includes a device that controls a diaphragm pump 522 to perform ATF through a hollow fiber filter 524 both of which are encased in a sterilizable housing 526. Medium and additives are introduced into the bioreactor 510 via a feed line 514, which is controlled by a valve and/or pump 516. An air supply source and controller are fluidly connected to the diaphragm pump 522 via an air tube 528. Air is added and withdrawn from the diaphragm pump 522 so as to increase and decrease the volume of the two chambers contained within the diaphragm pump, altering the pressure within the housing 526 and directing flow of the fluid contained within the housing 526 and drawing fluid across the membrane of the hollow fiber filter 524. Typically, the interior portion of the hollow fibers is fluidly connected to the bioreactor via drain tube 512 while the chamber outside the hollow fibers of the hollow fiber filter 524 and within the housing 526 is fluidly connected to a product drain tube 530. The product drain tube 530 has a harvest pump/valve 532 that controls withdrawal of the products that filter across the hollow fiber filter and reside in the chamber between the hollow fiber filter 524 and housing 526.

Continuous feeding can take place in low volume (less than 1.0 vessel volume exchanged per day (VVD), e.g., less than 0.7 VVD), and for a variable number of days (for example 2-8 days) prior to performing the rapid harvest. In one preferred embodiment a continuous slow feeding and harvesting (@ 0.5 VVD) takes place from day 11 to day 14 of cultivation. After the 72 hours simultaneous feeding and harvesting as rapid harvest occurs. The protein is harvested using the ATF 520 at a flux of 10-30 LMH (generally 12-18, 13-16, or 15 LMH) until the volume of the bioreactor 510 drops down below 20% (preferably <10%), substantially harvesting the liquid portion of the bioreactor. The rapid harvest part of the process takes approximately 3 hours to complete for the size bioreactor shown.

The continuous feeding and rapid harvest process has significant advantages. The methods described earlier in this disclosure require 14 days culture and approximately 6 hours of additional harvest time, resulting in final amount of recovered protein. In the continuous feeding and rapid harvest process using ATF there are 11 days of regular culture followed by 3 days continuous feed/harvest (for the same total of 14 days) follow by only 3 hours of rapid harvest. This process results in an increased amount of protein recovered in substantially the same amount of time from the same bioreactor equipment used in fed batch culture production. In addition, the continuous feed during low volume harvest prior to rapid harvest maintains or improves cell viability and product quality better than currently available process technology.

In all of the embodiments described for rapid harvest the final product pool can further be concentrated by use of the ATF with an ultrafilter to reduce volume for subsequent additional processing or storage of the product.

EXAMPLES

The invention is further described in the following examples, which do not limit the scope of the invention described in the claims.

1) ATF Rapid Harvest Using Step-Diafiltration—Traditional Fed-Batch

A variety of testing and experimental procedures were required to improve a fed-batch rapid harvesting system with use of ATF step-diafiltration. Examples include a 6 L fed-batch bioreactor (with an ATF2 system from Repligen Corp., Waltham Mass.) for rapid harvesting. ATF2 data was used to extrapolate to a 1000 L fed-batch bioreactor (with an ATF10 system from Repligen Corp., Waltham Mass., a commercially available perfusion product for 500 L and 1000 L bioreactors).

Testing was also carried out to determine the percentage recovery and total harvest time for this method. For this testing, a frozen vial of LONG®R3IGF-1 adapted CHO DP12 cells was thawed and grown in 125 mL shake flask (working volume 40 mL) containing CD OptiCHO® medium with 100 ng/mL LONG® R3IGF-1, 200 nM Methotrexate and 4 mM Glutamax®. After 4-6 days, the cells were passaged/sub cultured again into a 1 L (working volume 200 mL) shake flask in order to generate sufficient number of cells to be inoculated into the bioreactor. Once the density reached 5-7E6 cells/mL, the cells were inoculated into 3 L bioreactor (working volume 1.5 L) assembled with SS-ATF2. Feeding strategies and bioreactor conditions for fed-batch bioreactor are described in the Tables 2 and 3.

TABLE 2

Fed-Batch Conditions
Fed-Batch Conditions

| | |
|---|---|
| Cell Lines | CHO DP12 (ATCC CRL-12445 ™) |
| Media | CD OptiCHO ™ Medium |
| Media supplements | LONG ®R3 IGF-I (100 ng/mL) |
| | Methotrexate (200 nM)* |
| | Glutamax (4 mM) |
| Feeds | Day 3: Feed A (5%) + Feed B (5%) |
| | Day 6: Feed A (5%) + Feed B (5%) |
| | Day 9: Feed A (5%) + Feed B (5%) |
| | Day 12: Feed A (5%) + Feed B (5%) |
| Glucose Feeds | No glucose feeds |
| | (Feeds already contain high concentrations) |
| Seeding Density | 0.4 E6/mL |
| Working Volume (Day 0) | Bioreactor: 1200 mL |
| Working Volume (End day) | Bioreactor: 2000 mL |
| Antibody Product | Human Anti-IL-8 |

Note*:
Methotrexate was used only for seed expansion and not in the Fed-batch cultures

TABLE 3

Bioreactor Conditions
Bioreactor Conditions

| Conditions | Mode | Set point | Controlled by |
|---|---|---|---|
| Temperature | AUTO | 37° C. | Heating Blanket |
| Agitation | AUTO | 280 rpm | Stirrer |
| pH | AUTO | 6.8-7.2 | $CO_2$ and |
| DO | AUTO | 40% | $O_2$ supplement |
| Air | Manual | 500 mL/min | Constant |

On day 14, at the end of fed-batch culture the harvesting process was started at ATF rate of 0.9 LPM and a flux of 15 LMH. After each cycle (as shown in FIG. 1), the bioreactor was filled with sterile PBS back to 100%, and a second harvesting cycle was started at same flux to recover the remaining amount of IgG. Similarly, another cycle (total 3 cycles) was repeated in similar fashion.

Figure 3:
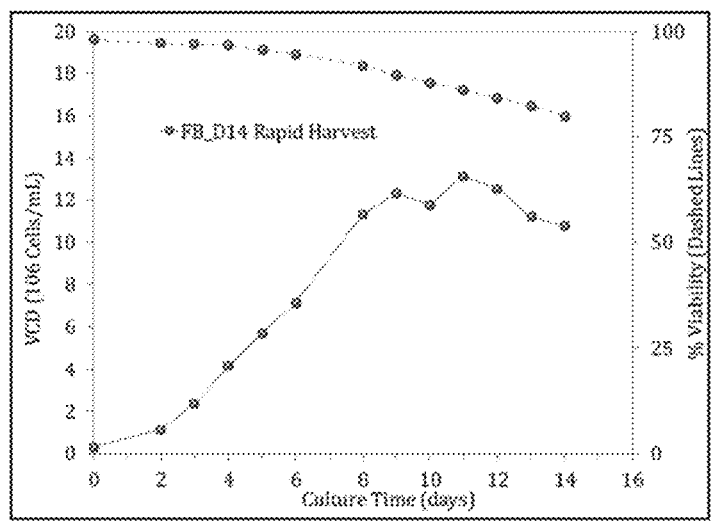
FIG. 3 is a plot of viable cell density (VCD) and viability as a function of culture time using the method of FIG. 1.

FIG. 3 shows the resulting plot of viable cell density (VCD) and viability as a function of culture time. These are typical profiles in fed-batch cultures and generally the viability on the day of harvest varies between 60-85%. The maximum VCD was ~14 E6 cells/mL and the VCD at the day of harvest was 9-10E6 cells/mL.

Figure 4:
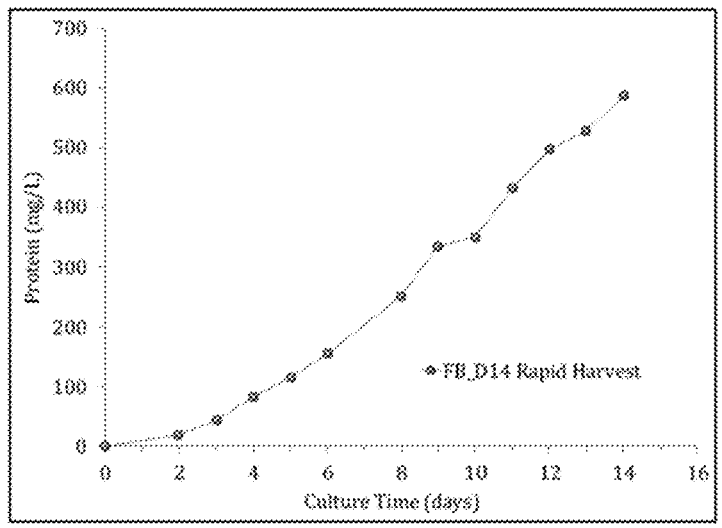
FIG. 4 is a plot of protein concentration as a function of culture time using the method of FIG. 1.

FIG. 4 is a plot of concentration of protein in fed-batch culture from day 1 through day 14. The final concentration of protein on the day of harvest was ~600 mg/L and this was used as an initial concentration before starting the rapid harvest process.

Figure 5:
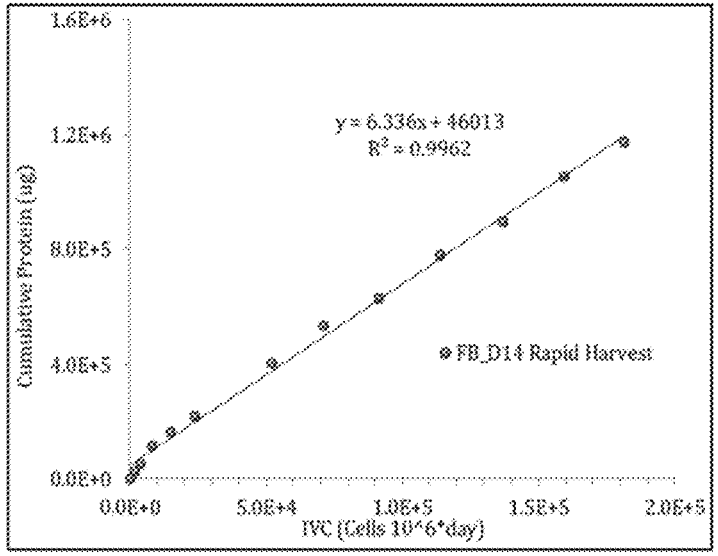
FIG. 5 is a plot of cell-specific productivity based on cumulative protein as a function of the integral of viable cell count (IVC) using the method of FIG. 1.

FIG. 5 is a plot of cell-specific productivity or cumulative protein as a function of cell growth over time, i.e., the integral of viable cells (IVC). The linear plot between IVC and cumulative protein indicates that cells specific productivity remains approximately the same throughout the fed-batch process.

Generally in fed-batches, harvest clarification is achieved by centrifugation followed by depth filtration. This is a two-step process as usage of depth filter alone is currently unable to handle high-solids feed streams (especially when cell densities are high) and are often have to use in series with centrifugation. In addition, depth filtration has limitations in terms of scale-up and monitoring differential pressures.

On the other hand, using ATF step-diafiltration, the entire process can be combined to a single step with shorter duration. ATF with 0.2 μm micro filter is well suited for harvesting a fed batch culture because it retains cells and also other small particulates, which are beneficial for downstream processes. Using ATF also reduces cross contamination as the harvesting can be conducted in a sterile manner. The commercially available ATF10 system can provide ATF perfusion for 500 L and 1000 L bioreactors, and can be used in multiples to easily scale up to 2000 L bioreactors. Based on the data described herein, protein recoveries can be over 95% using rapid harvest using step-diafiltration.

The overall time for harvesting process using ATF step-diafiltration is less than 8 hours. No significant drop in viability indicates that protein quality does not alter during harvesting process. The resulting viability and IgG concentrations after each cycle of harvesting are shown in Table 4 below. After each cycle, samples were collected from the bioreactor to measure viability and protein concentrations. No sample was collected after the first cycle (ND=Not Determined).

TABLE 4

Viability and IgG Concentrations

| Conditions | % Viability | Titer in BR (mg/L) | % Recovery | Time (hrs.) |
|---|---|---|---|---|
| End of FB-Day 14 | 80 | 587 | NA | NA |
| After 1st Cycle | ND | ND | ND | 2-2.5 |
| After 2nd Cycle | 75 | 98 | 83% | 2-2.5 |
| After 3rd Cycle | 71 | 21.5 | 96% | 2-2.5 |

Two ATF10 bioreactors can be run simultaneously. Each ATF10 has 11 $m^2$ surface area and when they are used simultaneously the total combined area is 22 $m^2$. The total harvesting time can be further shortened by increasing the number of ATF10 devices from 2 to 3 or more.

The following Table 5 was tabulated based on the surface area from ATF2 to mid-sized (2.5 $m^2$ surface area) ATF6 to the ATF10.

TABLE 5

Scale-Up Calculations

| Fed-Batch BR (L) | ATF | ATF SA (M2) | Flux (LMH) | ATF Rapid harvest process using Step-Diafiltration | | | Total Time for harvest (hr) | Final Harvest Volume (L) |
|---|---|---|---|---|---|---|---|---|
| | | | | $1^{st}$ Cycle: Vol down to 20% (min) | $2^{nd}$ Cycle: Vol down to 20% (min) | 3rd Cycle: Vol down to 20% (min) | | |
| 6 | ATF2 | 0.13 | 15 | 147.7 | 147.7 | 147.7 | 7.4 | 14.4 |
| 115 | ATF6 | 2.5 | 15 | 147.2 | 147.2 | 147.2 | 7.4 | 276 |
| 500 | ATF10 | 11 | 15 | 145.5 | 145.5 | 145.5 | 7.3 | 1200 |

TABLE 5-continued

Scale-Up Calculations

| Fed-Batch BR (L) | ATF | ATF SA (M2) | Flux (LMH) | ATF Rapid harvest process using Step-Diafiltration | | | Total Time for harvest (hr) | Final Harvest Volume (L) |
|---|---|---|---|---|---|---|---|---|
| | | | | 1st Cycle: Vol down to 20% (min) | 2nd Cycle: Vol down to 20% (min) | 3rd Cycle: Vol down to 20% (min) | | |
| 1000 | ATF10 | 11 | 15 | 290.9 | 290.9 | 290.9 | 14.5 | 2400 |
| 1000 | 2XATF10 | 22 | 15 | 145.5 | 145.5 | 145.5 | 7.3 | 2400 |
| 2000 | 2XATF10 | 22 | 15 | 290.9 | 290.9 | 290.9 | 14.5 | 4800 |
| 2000 | 4XATF10 | 44 | 15 | 145.5 | 145.5 | 145.5 | 7.3 | 4800 |

In these experiments, ATF2 with a 6 L fed-batch bioreactor at a flux of 15 LMH was successfully demonstrated to harvest protein in less than 8 hours with recovery of 96% of the product. Extrapolating the surface area from ATF2 (0.13 m$^2$) to ATF10 (11 m$^2$), allows one to predict that a 500 L fed-batch bioreactor can be rapidly harvested within 8 hours using an ATF10 according to the methods described herein. Similarly, a 1000 L fed-batch bioreactor can be harvested in 8 hours using two ATF10s (total filter surface area (SA): 22 m$^2$). In addition, there was minimal loss in viability during the harvesting process.

2) ATF Rapid Harvest Using Continuous Diafiltration—Traditional Fed-Batch

To evaluate the rapid harvesting technique, a 2 L fed-batch bioreactor connected to ATF2 was used to mimic a 6 L fed-batch bioreactor using a scale down model (SDM), recirculation approach. A 6 L bioreactor with ATF2 data was used to extrapolate to 500 L and 1000 L fed-batch bioreactor using an ATF10.

Testing was also carried out to determine the percentage recovery and total harvest time for this method, similar to in the previously described method.

Figure 9:
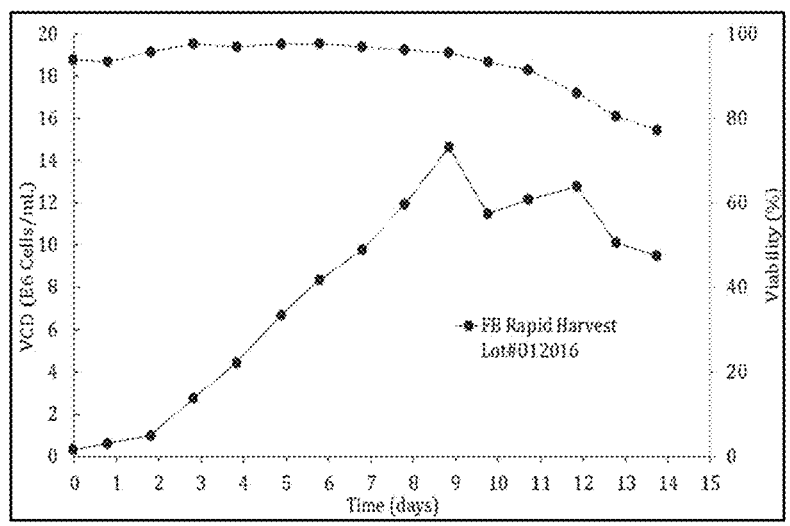
FIG. 9 is a plot of viable cell density and viability as a function of culture time using the method of FIG. 7.

FIG. 9 shows the resulting plot of viable cell density (VCD) and viability as a function of culture time. These are typical profiles in fed-batch cultures and generally the viability on the day of harvest varies between 60-85%. The maximum VCD was ~14E6 cells/mL and the VCD at the day of harvest was 9-10E6 cells/mL.

Figure 10:
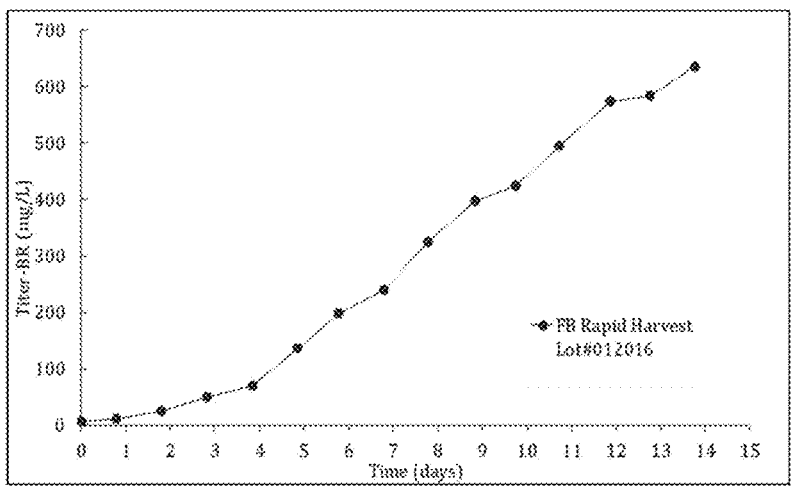
FIG. 10 is a plot of protein concentration as a function of culture time using the method of FIG. 7.

FIG. 10 is a plot of protein or titer content is a plot of concentration of protein in fed-batch culture from day 1 through day 14. The final concentration of protein on the day of harvest was ~600 mg/L and this was used as an initial concentration before starting the rapid harvest process.

Figure 11:
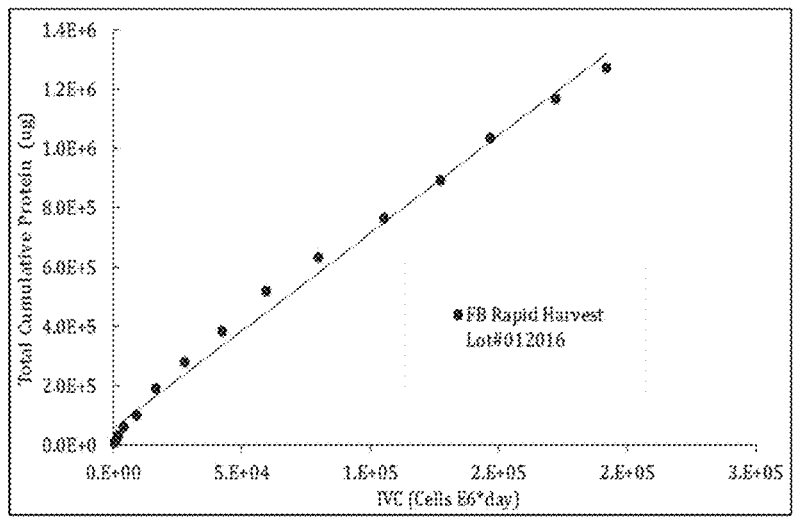
FIG. 11 is a plot of cell-specific productivity based on cumulative protein as a function of the integral of viable cell count using the method of FIG. 7.

FIG. 11 is a plot of cell-specific productivity or cumulative protein as a function of cell growth over time, i.e., the integral of viable cells (IVC). The linear plot between IVC and cumulative protein indicates that cells specific productivity remains same throughout the fed-batch process.

Generally, in fed-batches, harvest clarification is achieved by centrifugation followed by depth filtration. This is a two-step process as usage of depth filter alone is currently unable to handle high-solids feed streams (especially when cell densities are high) and are often have to use in series with centrifugation. In addition, depth filtration may have limitations in terms of scale-up and monitoring differential pressures.

On the other hand, using ATF continuous-diafiltration, the entire process can be combined to a single step with even shorter duration than the ATF step-diafiltration process. ATF with 0.2 µm microfilter is well suited for harvesting a fed batch culture because it retains cells and also other small particulates, which if removed are beneficial for downstream processes. Using ATF also reduces cross contamination as the harvesting can be demonstrated in a sterile manner. The systems described herein can be scaled up to 500, 1000, 1500, or 2000 L, for example, using two or more ATF10 perfusion products (Repligen, Waltham Mass.). Based on the data described herein, the protein recoveries can be better than 95% using rapid harvest using step-diafiltration.

The overall time for harvesting process using ATF continuous diafiltration is less than 6 hours. No significant drop in viability indicates that protein quality does not alter during harvesting process.

The resulting recovery and IgG concentrations after each cycle of harvesting are shown in Table 6 below.

TABLE 6

Recovery and IgG Concentrations

| Conditions | Volume (mL) | IgG Conc | Total Protein (mg) |
|---|---|---|---|
| BR-Before Harvesting | 1600 | 635.1 | 1016.2 |
| Harvest bag- After Completion of rapid harvest | 3250 | 297.5 | 966.9 |
| Recovery | | Recovery | 95% |

The recovery of protein after rapid harvest using continuous diafiltration is shown in Table 7 below.

TABLE 7

Protein Recovery

| | Time (Hrs) | BR Volume + ATF | % Viability | Titer in BR (mg/L) | Flux |
|---|---|---|---|---|---|
| Process | Day 14 Fed-Batch | 1600 | 77 | 635.1 | NA |
| Volume down To 30% | 0.17 | 1513 | 79.6 | 636.9 | 15 |
| | 1.00 | 1160 | 69.4 | 638.7 | 15 |
| | 2.00 | 550 | 73.7 | 658.4 | 15 |
| Diafiltration | | | | | |
| Continuous Diafiltration at 30% volume | 3.33 | 550 | 73 | 178.3 | 15 |
| | 4.67 | 550 | 72.9 | 43.0 | 15 |
| | 6.00 | 550 | 70.6 | 16.23 | 15 |

Data using the ATF2 and ATF6 results were extrapolated to the larger ATF10. It was determined that a 500 L fed-batch bioreactor can be harvested in less than 6 hours using ATF10, and 1000 L fed-batch bioreactor can be harvested with two ATF10s (total filter surface area (SA): 22 m$^2$). Table 8 was tabulated based on the surface area from ATF2 to ATF6 to ATF10.

TABLE 8

Scale up

| Fed-Batch BR (L) | ATF | ATF SA (m2) | Flux (LMH) | Before Difiltr. Vol down to 30% (hr) | Continuous-Diafiltration (4 cycles) | | | | Total Time for harvest (hr) | Final Harvest Volume (L) |
|---|---|---|---|---|---|---|---|---|---|---|
| | | | | | 1st | 2nd | 3rd | 4th | | |
| 6 | 1XATF2 | 0.15 | 15 | 2.15 | 0.9 | 0.9 | 0.9 | 0.9 | 5.8 | 11 |
| 115 | 1XATF6 | 2.5 | 15 | 2.15 | 0.9 | 0.9 | 0.9 | 0.9 | 5.8 | 219 |
| 500 | 1XATF10 | 11 | 15 | 2.12 | 0.9 | 0.9 | 0.9 | 0.9 | 5.8 | 950 |
| 1000 | 1XATF10 | 11 | 15 | 4.24 | 1.8 | 1.8 | 1.8 | 1.8 | 11.5 | 1900 |
| 1000 | 2XATF10 | 22 | 15 | 2.12 | 0.9 | 0.9 | 0.9 | 0.9 | 5.8 | 1900 |
| 2000 | 2XATF10 | 22 | 15 | 4.24 | 1.8 | 1.8 | 1.8 | 1.8 | 11.5 | 3800 |
| 2000 | 4XATF10 | 44 | 15 | 2.12 | 0.9 | 0.9 | 0.9 | 0.9 | 5.8 | 3800 |

ATF2 with a 6 L fed-batch bioreactor at a flux of 15 LMH was successfully demonstrated to harvest protein in less than 6 hours with recovery of 95%. Extrapolating the surface area from ATF2 (0.13 m$^2$) to ATF10 (11 m$^2$), allows one to predict that a 500 L fed-batch bioreactor can be rapidly harvested within 6 hours using an ATF10. Similarly, a 1000 L fed-batch bioreactor can be harvested in 6 hours using two ATF10s. In addition, there was no significant loss of viability during harvesting process.

3) ATF Rapid Harvest Using Continuous Diafiltration—Concentrated Fed-Batch

In CFB, it is recommended to drop the bioreactor volume only when VCD is less than 100E6 cells/mL. The following two tables were tabulated based on the surface area scaled from ATF2 to ATF6 to ATF10. The first table, Table 9, is considering the bioreactor volume reduction to 50% before starting the continuous diafiltration process. The second table, Table 10, is without reduction in bioreactor volume, i.e., the diafiltration starts from the beginning.

TABLE 9

Scale Up With 50% Reduction

| Fed-Batch BR (L) | ATF | ATF SA (m2) | Flux (LMH) | Before Difiltr. Vol down to 50% (hr) | Continuous-Diafiltration | | | | Total Time for harvest (hr) | Final Harvest Volume (L) |
|---|---|---|---|---|---|---|---|---|---|---|
| | | | | | 1st | 2nd | 3rd | 4th | | |
| 6 | ATF2 | 0.13 | 15 | 1.54 | 1.5 | 1.5 | 1.5 | 1.5 | 7.7 | 15 |
| 115 | ATF6 | 2.5 | 15 | 1.53 | 1.5 | 1.5 | 1.5 | 1.5 | 7.7 | 287.5 |
| 500 | ATF10 | 11 | 15 | 1.52 | 1.5 | 1.5 | 1.5 | 1.5 | 7.6 | 1250 |
| 1000 | ATF10 | 11 | 15 | 3.03 | 3.0 | 3.0 | 3.0 | 3.0 | 15.2 | 2500 |
| 1000 | 2XATF10 | 22 | 15 | 1.52 | 1.5 | 1.5 | 1.5 | 1.5 | 7.6 | 2500 |
| 2000 | 2XATF10 | 22 | 15 | 3.03 | 3.0 | 3.0 | 3.0 | 3.0 | 15.2 | 5000 |
| 2000 | 4XATF10 | 44 | 15 | 1.52 | 1.5 | 1.5 | 1.5 | 1.5 | 7.6 | 5000 |

TABLE 10

Scale Up With 0% Reduction

| Fed-Batch BR (L) | ATF | ATF SA (m2) | Flux (LMH) | Before Difiltr. Vol down to 0% (hr) | Continuous-Diafiltration | | | | Total Time for harvest (hr) | Final Harvest Volume (L) |
|---|---|---|---|---|---|---|---|---|---|---|
| | | | | | 1st | 2nd | 3rd | 4th | | |
| 6 | ATF2 | 0.13 | 15 | 0.00 | 3.1 | 3.1 | 3.1 | 3.1 | 12.3 | 24 |
| 115 | ATF6 | 2.5 | 15 | 0.00 | 3.1 | 3.1 | 3.1 | 3.1 | 12.3 | 460 |
| 500 | ATF10 | 11 | 15 | 0.00 | 3.0 | 3.0 | 3.0 | 3.0 | 12.1 | 2000 |
| 1000 | ATF10 | 11 | 15 | 0.00 | 6.1 | 6.1 | 6.1 | 6.1 | 24.2 | 4000 |
| 1000 | 2XATF10 | 22 | 15 | 0.00 | 3.0 | 3.0 | 3.0 | 3.0 | 12.1 | 4000 |
| 2000 | 2XATF10 | 22 | 15 | 0.00 | 6.1 | 6.1 | 6.1 | 6.1 | 24.2 | 8000 |
| 2000 | 4XATF10 | 44 | 15 | 0.00 | 3.0 | 3.0 | 3.0 | 3.0 | 12.1 | 8000 |

4) ATF Rapid Harvest Using Continuous Feeding

The FB with continuous feeding and rapid harvest process was developed to further shorten the harvesting time by half and increase protein production. This is achieved through a low volume continuous feed prior to rapid harvest together with a high flux rapid harvest. In the example described below a 40% increase in protein yield was obtained compared to currently existing commercially available fed-batch harvest techniques. In this example of continuous feeding and rapid harvest process using ATF there are 11 days of regular culture as described in other examples, followed by 3 days continuous feed/harvest (for the same total of 14 days) follow by only 3 hours of rapid harvest. Other embodiments could change the length of time for the continuous feed or the volume of the continuous feed to obtain similar improvements in cell viability and total protein production. For these tests a 2 L bioreactor with recirculation method was used to mimic 6 L fed-batch bioreactor, and flux was maintained at 15 LMH using recirculation approach.

Figure 15:
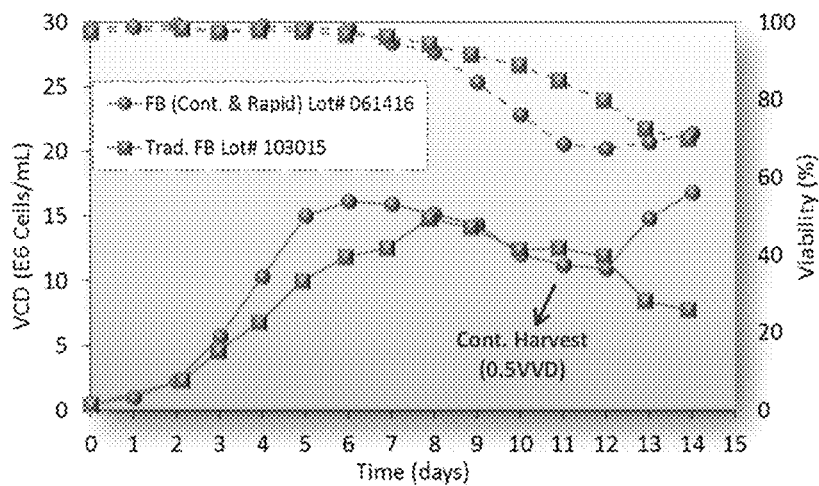
FIG. 15 is a plot of viable cell density and viability as a function of culture time using the method of FIG. 14 compared to traditional fed-batch processes.
Figure 16:
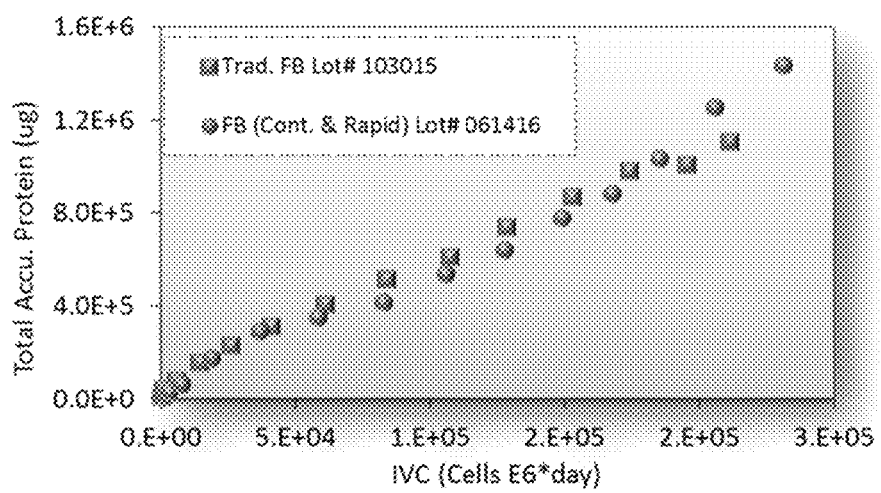
FIG. 16 is a plot of cell-specific productivity based on cumulative protein as a function of the integral of viable cell count using the method of FIG. 14 compared to traditional fed-batch processes.
Figure 17:
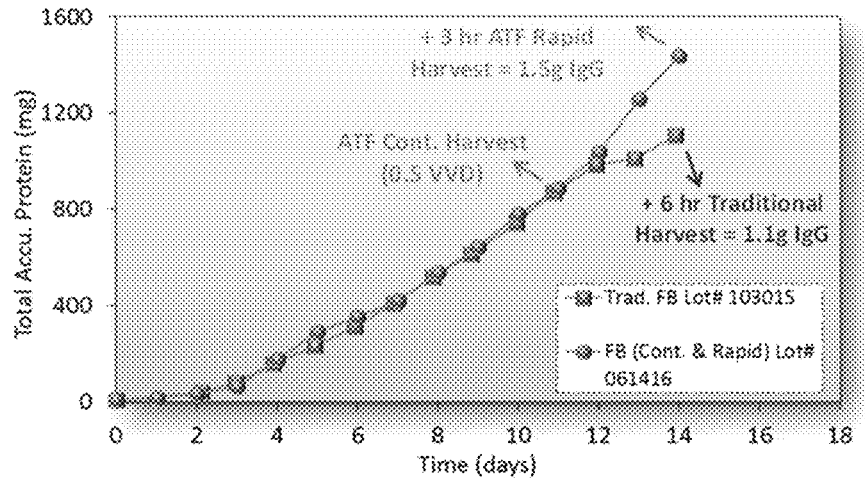
FIG. 17 is a plot of protein concentration as a function of culture time using the method of FIG. 14 compared to traditional fed-batch processes.

FIG. 15 shows the resulting plot of viable cell density (VCD) and viability as a function of culture time for both continuous feeding and traditional fed-batch. Both VCD and viability showed increasing trends following the onset of continuous feeding and harvest on day 11. FIG. 16 is a plot of cell-specific productivity or cumulative protein as a function of cell growth over time, i.e., the integral of viable cells (IVC) for both processes. FIG. 17 is a plot of protein in fed-batch culture from day 1 through day 14 showing increased total accumulation after continuous feeding and harvest started on day 11 compared to traditional fed-batch.

Table 11 shows the conditions used for the fed-batch harvest culture.

TABLE 11

Fed-Batch conditions
Fed-Batch Conditions

| Bioreactors | Traditional Fed-batch | Improved Fed-Batch with continuous feeding & rapid harvest using ATF |
|---|---|---|
| Cell Lines | CHO DP12 (ATCC CRL-12445 ™) | |
| Media | CD OptiCHO ™ Medium | |
| Media supplements | LONG ®R3 IGF-I (100 ng/mL) Methotrexate (200 nM)* Glutamax (4 mM) | |
| Feeding Strategies | Day 3: Feed A (5%) + Feed B (5%) Day 6: Feed A (5%) + Feed B (5%) Day 9: Feed A (5%) + Feed B (5%) | |
| | Day 12: Feed A (5%) + Feed B (5%) | Day 11-Day 14: 0.5 VVD perfusion rate for continuous harvest Day 14: 15 LMH for rapid harvest (no media feed) |
| Glucose Feeds | No glucose feeds (Feeds already contain high concentrations) | |
| Seeding Density | 0.4 E6/mL | |
| Working Volume (Day 0) | Bioreactor: 1200 mL | |
| Antibody | Human Anti-IL-8 | |

Note*:
Methotrexate was used only for seed expansion and not in the Fed batch cultures The resulting viability after each 0 to 3 hours of harvesting are shown in Table 12 below. VCD & viability measurements were conducted at approximately at 2.7 hours.

TABLE 12

VCD and Viability

| Process | Time points | Time (Hrs) | BR Volume + ATF | % Viability | VCD (E6/mL) | Titer in BR (mg/L) | Titer in HL (mg/L) | % Protein Passage | Flux | Harvest Bag IgG Conc. | Harvaest Bag (Volume m/L) | Harvest IgG (g) |
|---|---|---|---|---|---|---|---|---|---|---|---|---|
| ATF Rapid Harvest | Day 14 | 0 hr | 1600 | 71.2 | 16.82 | 340.3 | 328.3 | 96% | NA | 415.43 | 2450 | 1.02 |
| | | 1 hr | 1050 | 70.7 | 21.11 | 346.1 | 328.8 | 95% | 15 | 398.71 | 3000 | 1.20 |
| | | 2 hr | 500 | 72.9 | 34.1 | 362.8 | 334.5 | 92% | 15 | 391.12 | 3550 | 1.39 |
| | | 3 hr | 300* | 70.3* | 77.13* | 403.8 | 340.3 | 84% | 15 | 386.11 | 4000 | 1.54 |

The following scale up data was extrapolated ATF2 to ATF10 based on the surface area (SA) of filters:

TABLE 13

Scale Up With 0% Reduction

| Fed-Batch BR (L) | ATF | ATF SA (m2) | Flux (LMH) | Permeate (L/Day) | Permeate (mL/MIN) | Harvest (mL/MIN) | Time for Rapid Harvest Harvest (hr) | Final Harvest Volume (L) @0.5 VVD for 3 days |
|---|---|---|---|---|---|---|---|---|
| 6 | 1X ATF2 | 0.15 | 15 | 46.8 | 32.5 | 32.5 | 3.1 | 15 |
| 115 | 1X ATF6 | 2.5 | 15 | 900 | 625 | 625 | 3.1 | 288 |
| 500 | 1X ATF10 | 11 | 15 | 3960 | 2750 | 2750 | 3.0 | 1250 |
| 1000 | 1X ATF10 | 11 | 15 | 3960 | 2750 | 2750 | 6.1 | 2500 |
| 1000 | 2X ATF10 | 22 | 15 | 7920 | 5500 | 5500 | 3.0 | 2500 |
| 2000 | 2X ATF10 | 22 | 15 | 7920 | 5500 | 5500 | 6.1 | 5000 |
| 2000 | 4X ATF10 | 44 | 15 | 15840 | 11000 | 11000 | 3.0 | 5000 |

Figure 18:
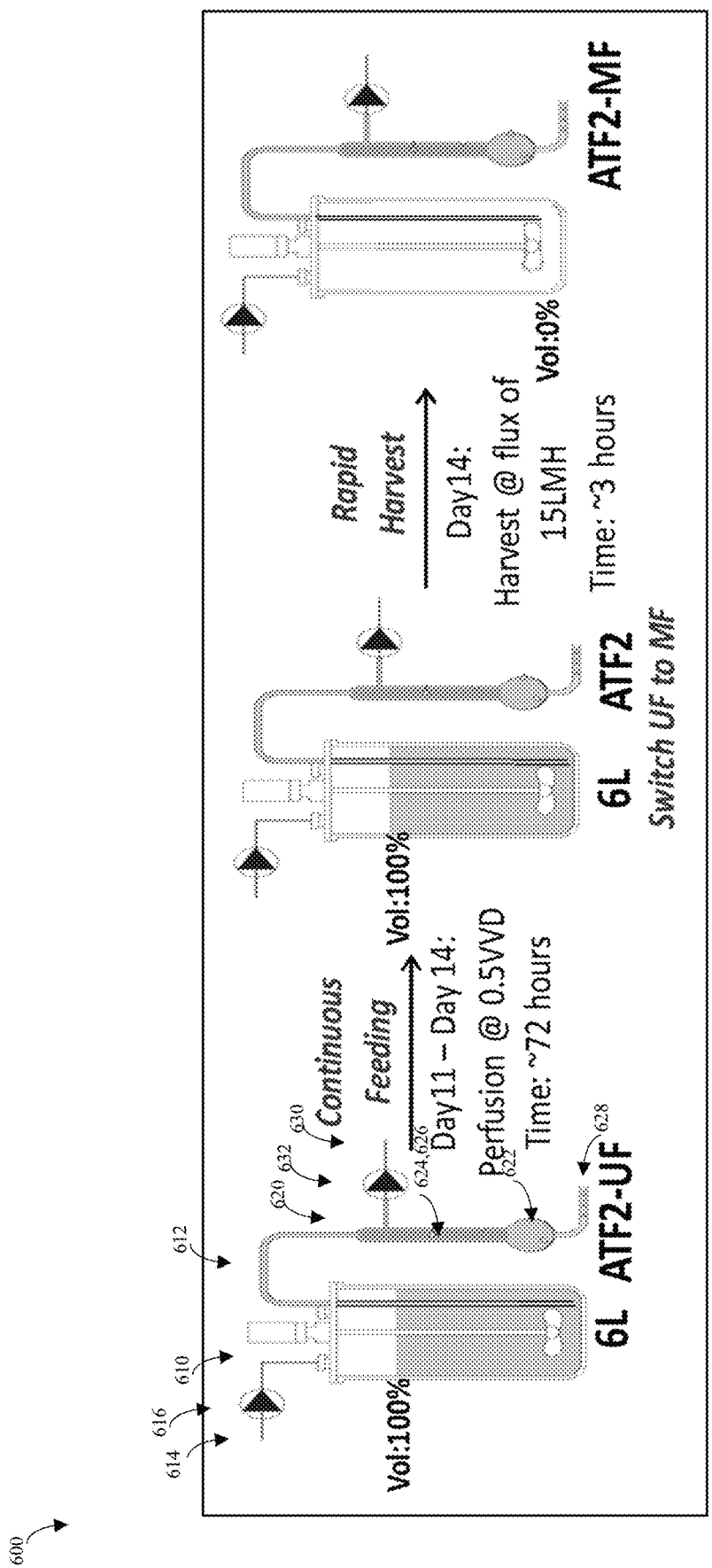
FIG. 18 is a schematic of an embodiment of an apparatus and process for performing ATF rapid harvest using continuous feeding with an ultra-filter.

The continuous feeding and rapid harvest process showed significant advantages. For this example, 11 days of regular culture followed by 3 days continuous feed/harvest followed by only 3 hours of rapid harvest obtained 1.4 times the amount of protein recovered by a conventional fed batch process. A process that can retain higher cell viability and yield higher protein production than currently available technology is a significant and meaningful process improvement As shown in FIG. 18, system 600 can carry out a process with continuous feeding while using the ATF equipped with an ultrafilter. Other elements of system 600 are the same as in prior embodiments. The product is retained in the bioreactor and all product is harvested during the rapid harvest phase. This further reduces the volume of the final product pool while still obtaining the increase product yield.

The following scale up data was extrapolated:

TABLE 14

Scale Up

| Fed-Batch BR (L) | ATF | ATF SA (m2) | Flux (LMH) | Permeate (L/Day) | Permeate (mL/MIN) | Harvest (mL/MIN) | Time for Rapid Harvest (hr) | Final Harvest Volume (L) |
|---|---|---|---|---|---|---|---|---|
| 6 | 1X ATF2 | 0.13 | 15 | 46.8 | 32.5 | 32.5 | 3.1 | 6 |
| 115 | 1X ATF6 | 2.5 | 15 | 900 | 625 | 625 | 3.1 | 115 |
| 500 | 1X ATF10 | 11 | 15 | 3960 | 2750 | 2750 | 3.0 | 500 |
| 1000 | 1X ATF10 | 11 | 15 | 3960 | 2750 | 2750 | 6.1 | 1000 |
| 1000 | 2X ATF10 | 22 | 15 | 7920 | 5500 | 5500 | 3.0 | 1000 |
| 2000 | 2X ATF10 | 22 | 15 | 7920 | 55000 | 5500 | 6.1 | 2000 |
| 2000 | 4X ATF10 | 44 | 15 | 15840 | 11000 | 11000 | 3.0 | 2000 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of harvesting a cell product from a fed batch culture using an alternating tangential flow (ATF) filter, the method comprising:
   producing a cell product in a fed batch culture until the cell product reaches a harvest concentration in the culture medium;
   harvesting the cell product by passing the culture medium through an ATF filter such that the cell product passes into a permeate channel of the ATF filter;
      wherein if the viable cell density is above a first value, the ATF filter is operated in diafiltration mode at a flux of 5-30 liters/meter$^2$/hour (LMH) until at least 90% of the cell product is in the permeate, and
      wherein, if the viable cell density is below the first value, the ATF filter is operated at a flux of 10-30 LMH in concentration mode until the viable cell density reaches the first value or the culture medium reaches a predetermined volume lower than the starting volume and thereafter operating in diafiltration mode until at least 90% of the cell product is in the permeate.

2. The method of claim 1, wherein harvesting takes less than 18 hours for a volume between 500 liters and 2000 liters.

3. The method of claim 2, the steps of wherein harvesting takes less than 6.0 hours.

4. The method of claim 1, wherein the ATF filter comprises a hollow fiber filter.

5. The method of claim 4, wherein the filter has a pore size of approximately about 0.1 to 5.0 microns or about 500 to 1000 kD.

6. The method of claim 1, wherein the cell product is a monoclonal antibody, enzyme, or virus.

7. The method of claim 1 wherein said diafiltration mode is step diafiltration or continuous diafiltration.

8. The method of claim 7, wherein diafiltration uses phosphate buffered saline as a replenishing liquid.

9. The method of claim 7, wherein diafiltration uses cell culture medium as a replenishing liquid.

10. The method of claim 1, wherein the predetermined volume is 5% to 30% of the starting volume.

11. The method of claim 10, wherein the predetermined volume is 10%-20% of the starting volume.

12. The method of claim 1, wherein the fed batch culture is a concentrated fed-batch culture, and wherein the predetermined volume is about 50% of the starting volume.

13. A system comprising:
   a bioreactor comprising an inlet and an outlet;
   a source of fluid medium containing no cell product connected to the bioreactor inlet;
   an alternating tangential flow (ATF) device connected to the bioreactor outlet;
   a pump connected to an outlet of the ATF device and configured to remove fluid from the ATF device;
   and a controller arranged and programmed to perform the method of claim 1.

14. The system of claim 13, wherein the ATF device comprises a hollow fiber filter.

15. The system of claim 14, wherein the filter has a pore size of approximately about 0.1 to 5.0 microns or about 500 to 1000 kD.

16. The system of claim 13, wherein the controller is arranged and programmed to set the predetermined volume to 5% to 30% of the starting volume.

17. The system of claim 13 wherein the ATF device operating in diafiltration mode is programmed for step diafiltration or continuous diafiltration.

18. The system of claim 13, wherein said predetermined value for viable cell density is 100e6.

* * * * *